United States Patent
Bradley

(10) Patent No.: US 7,072,715 B1
(45) Date of Patent: Jul. 4, 2006

(54) IMPLANTABLE CARDIAC STIMULATION DEVICE FOR AND METHOD OF MONITORING PROGRESSION OR REGRESSION OF HEART DISEASE BY MONITORING EVOKED RESPONSE FEATURES

(75) Inventor: Kerry Bradley, Glendale, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 10/637,850

(22) Filed: Aug. 7, 2003

Related U.S. Application Data

(63) Continuation of application No. 10/232,904, filed on Aug. 30, 2002, now abandoned, which is a continuation of application No. 09/691,689, filed on Oct. 18, 2000, now Pat. No. 6,473,647.

(51) Int. Cl.
*A61N 1/365* (2006.01)

(52) U.S. Cl. .......................................... 607/17; 607/28

(58) Field of Classification Search ................ 600/510; 607/4, 9–28
See application file for complete search history.

(56) References Cited

U.S. PATENT DOCUMENTS

| | | | | |
|---|---|---|---|---|
| 5,139,028 A | * | 8/1992 | Steinhaus et al. ........... | 600/510 |
| 5,197,480 A | * | 3/1993 | Gebhardt ..................... | 600/510 |
| 5,466,254 A | | 11/1995 | Helland ....................... | 607/123 |
| 5,643,327 A | | 7/1997 | Dawson et al. .............. | 607/24 |
| 5,674,254 A | * | 10/1997 | van Krieken ................. | 607/11 |
| 5,716,383 A | | 2/1998 | Kieval et al. ................. | 607/9 |
| 5,749,906 A | | 5/1998 | Kieval et al. ................. | 607/9 |
| 5,782,890 A | * | 7/1998 | Wahlstrand et al. .......... | 607/32 |
| 5,800,467 A | * | 9/1998 | Park et al. .................... | 607/17 |
| 5,902,324 A | * | 5/1999 | Thompson et al. ........... | 607/9 |
| 6,021,350 A | | 2/2000 | Mathson ...................... | 607/17 |
| 6,129,744 A | | 10/2000 | Boute .......................... | 607/25 |
| 6,148,230 A | * | 11/2000 | KenKnight ................... | 600/516 |
| 6,456,880 B1 | * | 9/2002 | Park et al. .................... | 607/25 |
| 6,473,647 B1 | * | 10/2002 | Bradley ........................ | 607/27 |
| 6,512,953 B1 | * | 1/2003 | Florio et al. .................. | 607/28 |
| 6,748,261 B1 | * | 6/2004 | Kroll et al. ................... | 600/510 |
| 6,823,213 B1 | * | 11/2004 | Norris et al. ................. | 607/9 |
| 2005/0033368 A1 | * | 2/2005 | Fishler et al. ................. | 607/9 |

OTHER PUBLICATIONS

Robert Pionsey, "Dependence of Scalar Potential Measurements on Electrode Geometry", The Review of Scientific Instruments, vol. 36, No. 7, Jul. 1965.

* cited by examiner

*Primary Examiner*—Robert E. Pezzuto
*Assistant Examiner*—Kristen Mullen

(57) ABSTRACT

An implantable cardiac stimulation device has a system and method that monitors progression or regression in a patient's heart disease. A pulse generator delivers pacing pulses to the heart to cause evoked responses of the heart. A sensing circuit senses the evoked responses of the heart and generates evoked response signals. A processor is programmed to analyze the evoked response signals, to isolate a given characteristic of the evoked response signals and to quantify the isolated characteristics to provide corresponding quantized values. Relative changes in the quantized values over time are indicative of the progression or regression in the patient's heart disease. A memory stores the quantized values and a telemetry circuit transmits the stored quantized values to an external receiver for analysis.

18 Claims, 5 Drawing Sheets

IMPLANTABLE CARDIAC STIMULATION DEVICE FOR AND METHOD OF MONITORING PROGRESSION OR REGRESSION OF HEART DISEASE BY MONITORING EVOKED RESPONSE FEATURES

CROSS-REFERENCE TO RELATED APPLICATIONS

This application is a continuation of U.S. patent application Ser. No. 10/232,904, now abandoned, which is a continuation of U.S. patent application Ser. No. 09/691,689, filed Oct. 18, 2000, now U.S. Pat. No. 6,473,647.

FIELD OF THE INVENTION

The present invention is generally directed to an implantable device for monitoring the progression or regression of heart disease. The present invention is more particularly directed to a system and method for use in an implantable cardiac stimulation device, which quantifies and stores evoked response features. Relative changes in the quantified evoked response features, over time, are indicative of the progression or regression of the heart disease.

BACKGROUND OF THE INVENTION

More people die of heart disease than any other single cause. One common form of heart disease is congestive heart failure.

Congestive heart failure (CHF) is a debilitating, end-stage disease in which abnormal function of the heart leads to inadequate bloodflow to fulfill the needs of the body's tissues. Typically, the heart loses propulsive power because the cardiac muscle loses capacity to stretch and contract. Often, the ventricles do not appropriately fill with blood between heartbeats and the valves regulating blood flow may become leaky, allowing regurgitation or back-flow of blood. The impairment of arterial circulation deprives vital organs of oxygen and nutrients. Fatigue, weakness, and inability to carry out daily tasks may result.

Not all CHF patients suffer debilitating symptoms immediately. Some may live actively for years. Yet, with few exceptions, the disease is relentlessly progressive.

As CHF progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles to grow in volume in an attempt to pump enough blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in ventricular filling.

Current standard treatment for heart failure is typically centered around medical treatment using ACE inhibitors, diuretics, and digitalis. It has also been demonstrated that aerobic exercise may improve exercise tolerance, improve quality of life, and decrease symptoms. Only an option in 1 out of 200 cases, heart transplantation is also available. Other cardiac surgery is also indicated for only a small percentage of patients with particular etiologies. Although advances in pharmacological therapy have significantly improved the survival rate and quality of life of patients, patients who are refractory to drug therapy have a poor prognosis and limited exercise tolerance. Cardiac pacing has been proposed as a new primary treatment for patients with drug-refractory CHF.

In patients with heart failure and atrial fibrillation (AF), the heart has often remodeled due to the disease, such that there is interstitial fibrosis and myocyte lengthening. There is also decreased myocyte density with increased collagenation in the connective structure of the myocardium. There is further abnormal calcium handling at both the sarcoplasmic reticulum and membrane levels. Manifestations of these effects are increased fractionation of heart electrical activity, decreased conduction velocity, and increased heterogeneity of repolarization.

Bi-chamber pacing (biventricular or biatrial) has been proposed as an emerging therapy for the treatment of heart failure and atrial fibrillation. The patients who appear to gain the greatest benefit from this pacing therapy are those with the greatest dyssynchrony, since the benefit of bi-chamber pacing appears dependent upon chamber synchronization and/or appropriate sequencing.

It is desirable to have a system, which would track the progression or regression of the patient's disease, particularly as it relates to the success of any therapy in halting or reversing the remodeling. By tracking the progression or regression of heart disease, such as CHF, more closely, treatments could be managed more effectively. Commonly, patients with heart disease have an implanted cardiac stimulation device. Hence, it would be advantageous if the implanted cardiac stimulation device were able to aid in the tracking of the progression or regression of the heart disease. The present invention provides a system and method for use in such a device capable of tracking heart disease progression or regression.

SUMMARY OF THE INVENTION

The present invention provides a system and method, for use in an implantable cardiac stimulation device, for monitoring progression or regression in heart disease such as congestive heart failure. In accordance with the present invention, isolated features in evoked responses of a heart are quantified and stored in a memory over time to monitor or track the progression or regression in a patient's heart disease, such as CHF. The evoked response, especially when stimulated and sensed in a unipolar configuration, is well suited to measurement of myocardial status since it measures the course of the action potentials of the group of cells in the region of stimulation immediately beneath and surrounding the stimulation electrode. Use of the evoked response is likened to a controlled experiment since, during stimulation, propagation of the wavefront spreads out from the stimulation point, a fixed, consistent region relative to the stimulation electrode.

Hence, in accordance with the present invention, a pulse generator delivers pacing pulses to the heart to cause evoked responses of the heart. The evoked responses are sensed by a sensing circuit to generate evoked response signals which are analyzed by isolating a given feature of the evoked responses and quantifying the isolated features to provide quantified values. The quantified values are stored in a memory over time and then conveyed by a telemetry circuit to an external receiver for analysis of the progression or regression of the heart disease.

The isolated features may be: the positive slope of the evoked response (which is related to conduction velocity); evoked response continuity (which is related to fractionation); evoked response maximum positive or negative amplitudes (which are related to myocardium wall thickness and dilation); or T-wave slope and amplitude (which are related to heterogeneity of repolarization).

The monitoring of the disease progression or regression may be performed for either one of the ventricles, or both, or either one of the atria, or both. The quantified values may further be employed by the implantable cardiac stimulation device for automatic adjustment of pacing parameters.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
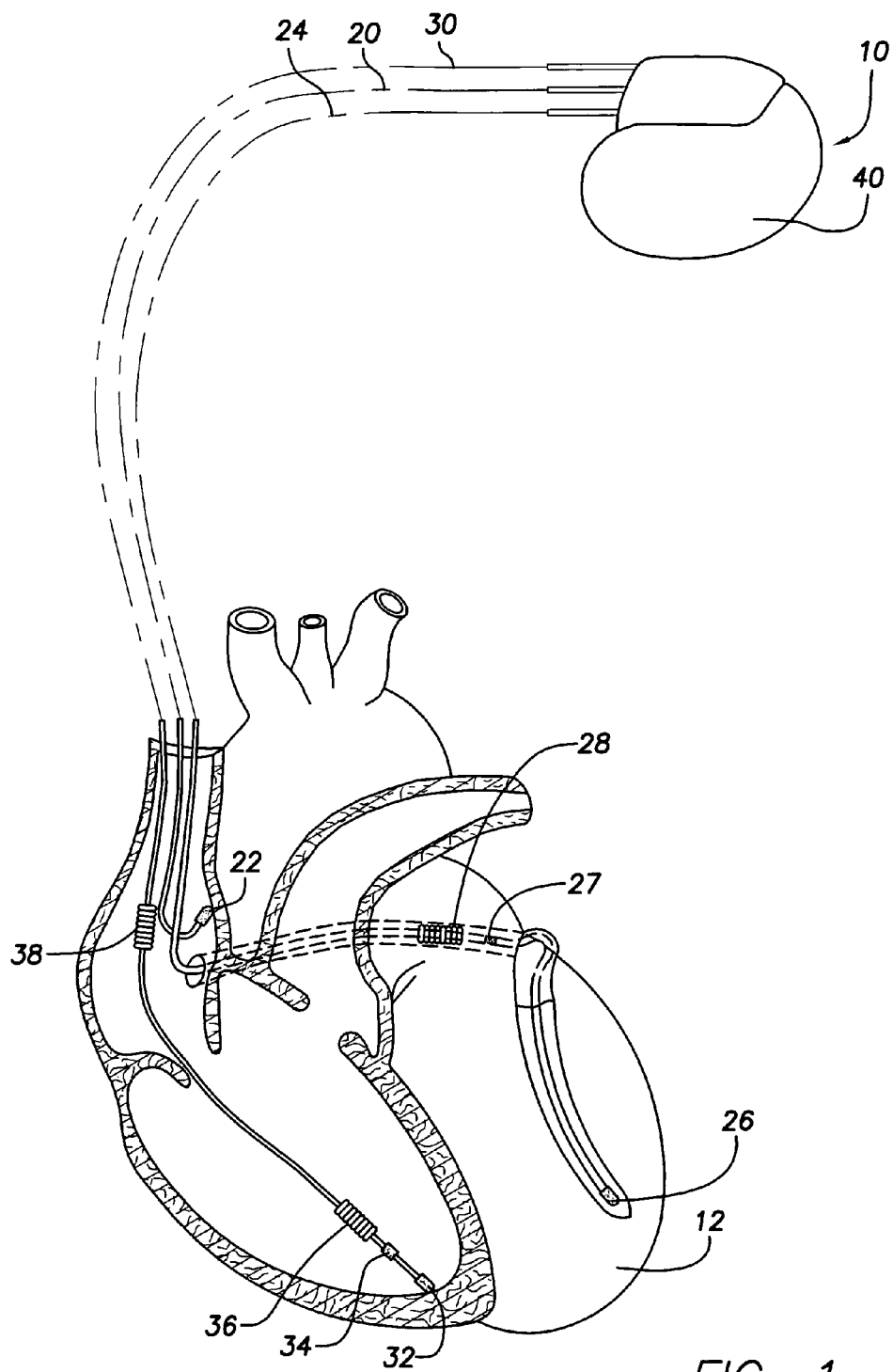
FIG. 1 is a simplified diagram illustrating an implantable stimulation device embodying the present invention in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, filed Dec. 8, 1999, entitled A SELF-ANCHORING, STEERABLE CONARY SINUS LEAD (Pianca et. al); and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
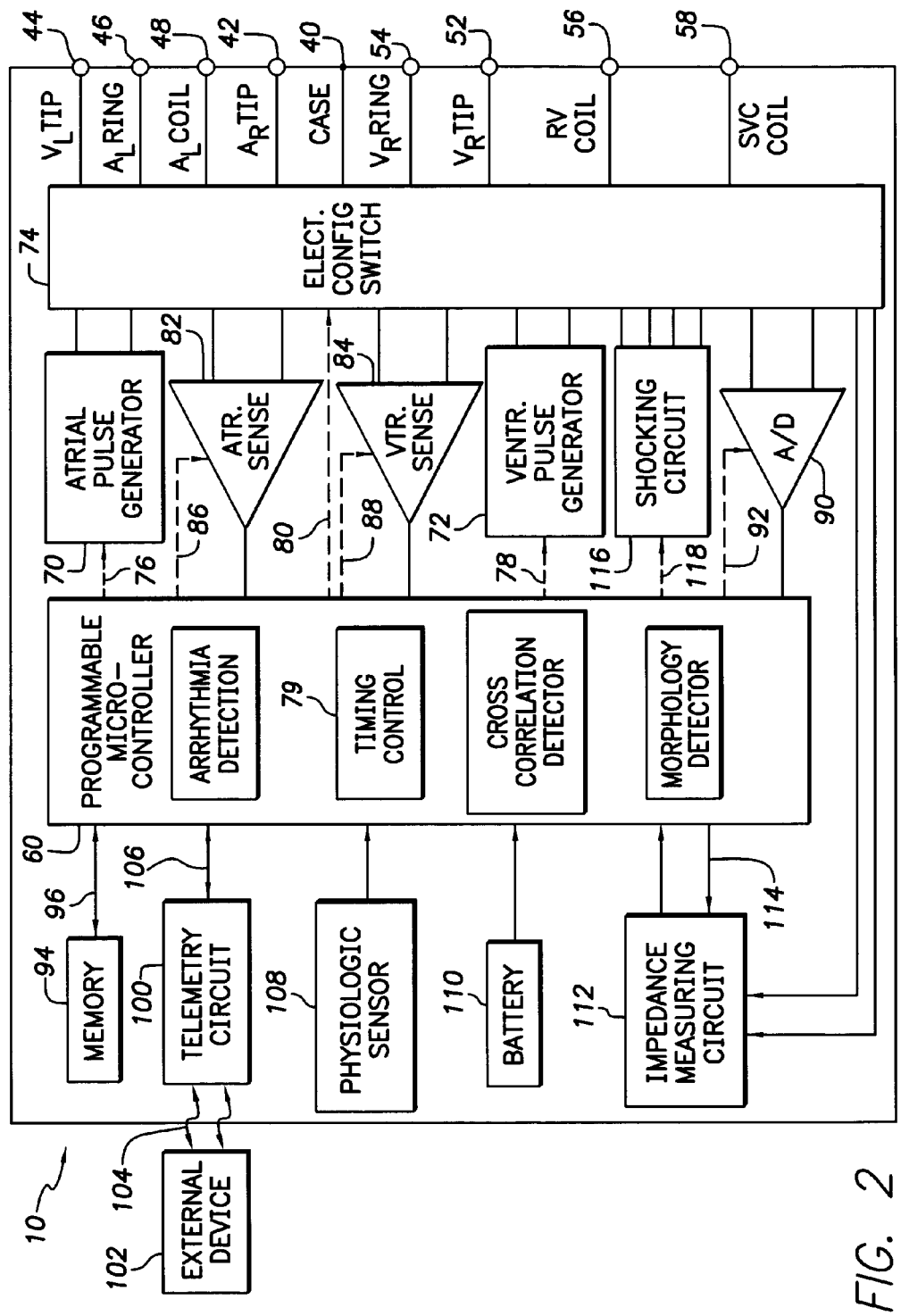
FIG. 2 is a functional block diagram of the device of FIG. 1 illustrating the basic elements for monitoring evoked responses in accordance with the present invention and providing cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the atrial tip electrode 22.

To achieve left chamber sensing, pacing and shocking, the connector includes at least a left ventricular tip terminal 44, a left atrial ring terminal 46, and a left atrial shocking terminal 48, which are adapted for connection to the left ventricular tip electrode 26, the left atrial tip electrode 27, and the left atrial coil electrode 28, respectively.

To support right chamber sensing, pacing and shocking, the connector further includes a right ventricular tip terminal 52, a right ventricular ring terminal 54, a right ventricular shocking terminal 56, and an SVC shocking terminal 58, which are adapted for connection to the right ventricular tip electrode 32, right ventricular ring electrode, 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes a timing control 79 which is used to control the timing of such stimulation pulses (e.g., pacing rate, atrioventricular (AV) delay, atrial interconduction (A—A) delay, or ventricular interconduction (V—V) delay, etc.) as well as to keep track of the timing of refractory periods, blanking periods, noise detection windows, evoked response windows, alert intervals, marker channel timing, etc., which is well known in the art.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74 for detecting the presence of cardiac activity in each of the four chambers of the heart. Accordingly, the atrial and ventricular sensing circuits, 82 and 84, may include dedicated sense amplifiers, multiplexed amplifiers, or shared amplifiers. The switch bank 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity, respectively, in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 84, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

In accordance with this preferred embodiment, the data acquisition system 90 is coupled to the microoontroller via appropriate control signal 92 and senses evoked responses from the heart 12 in response to applied stimulation pulses. The evoked response signals generated by the data acquisition system 90 are stored in a memory 94 by the microcontroller for processing by the microcontroller. More specifically, the microcontroller isolates a given feature from each evoked response signal generated by the data acquisition system 90 and quantifies the feature. The quantified feature value is then stored in memory 94. This process is repeated at regular intervals, as often as with every beat, or less often, as once or twice each day. Over time, the stored quantified values, and relative changes therein, are indicative of the progression or regression of the patient's heart disease, such as CHF. Specific evoked response features, which may be quantified for monitoring the progression or regression in the patients heart disease, in accordance with this embodiment, will be described in detail subsequently.

The microcontroller 60 is coupled to the memory 94 by a suitable data/address bus 96. In addition to the quantified evoked response feature values, the memory 94 may store programmable operating parameters used or modified by the microcontroller 60, as required, in order to control the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. A feature of the present invention is the ability of the microcontroller to modify or adjust the programmable parameters in response to the quantified evoked response feature values to titrate therapy delivered to the patient by the device.

Advantageously, initial operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through the established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110, which provides operating power to all of the circuits shown in FIG. 2. For the stimulation device 10, which employs shocking therapy, the battery must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 employs lithium/silver vanadium oxide batteries, as is true for most (if not all) such devices to date.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 by a control signal 114. The impedance measuring circuit 112 has many known uses. However, it is not critical to the present invention and is therefore shown only for completeness.

It is the primary function of the device 10 to function as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
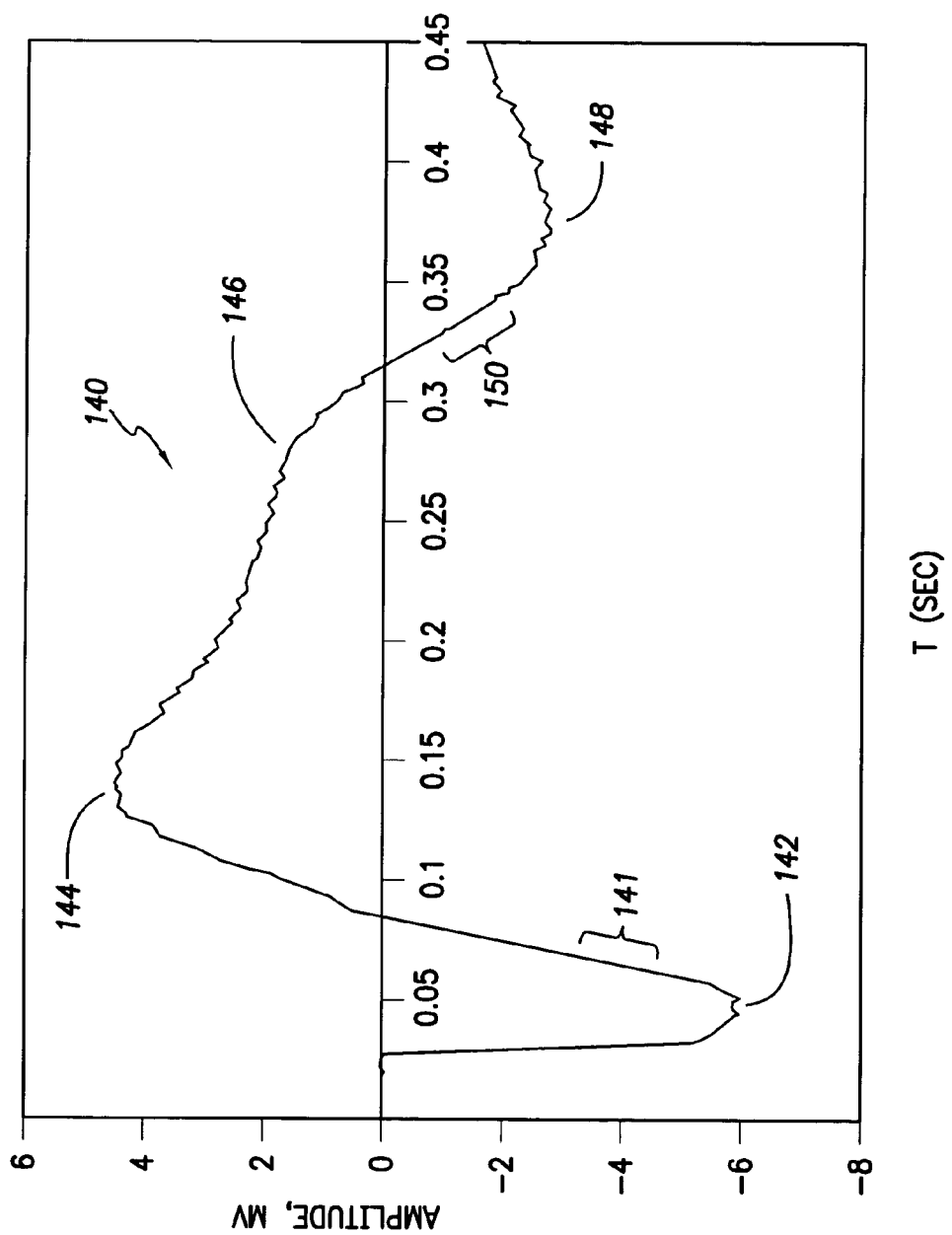
FIG. 3 is a typical unipolar ventricular evoked response identifying possible features, which may be extracted and quantified in accordance with the present invention.

FIG. 3 shows a typical unipolar ventricular evoked response 140\* identifying exemplary features, which may be extracted and quantified in accordance with the present invention. As previously discussed, the quantified evoked response feature values generated over time by the microcontroller are indicative of the progression or regression of the patient's heart disease, such as CHF. The evoked response features, which may be quantified to this end relate to conduction velocity, fractionation, wall thickness, and heterogeneity of repolarization.

Measurements of conduction velocity may be estimated from the positive slope 141 of the evoked response. If the evoked response is modeled as propagation of the depolarization wavefront away from the stimulation electrode, and the wavefront is modeled as a moving dipole, then the potential at the measurement electrode (ideally the pacing electrode) is inversely related to the conduction velocity of the myocardial tissue. If the conduction velocity is increased, the slope of the evoked response will increase and if the conduction velocity is decreased, the slope of the evoked response will decrease. Measurements of conduction velocity may be used to infer ANS tone as it effects the myocardium. Similarly, it may be used to assess the effectiveness of drug therapy administered by the physician.

With respect to fractionation, if the conduction away from the stimulation electrode is slowed through an area relative to other areas measured by the evoked response, then the evoked response will become fractionated. As fractionation occurs, the evoked response may appear discontinuous (more jagged) or less smooth. The degree of fractionation relates to the degree of continuity of the evoked response and may be quantified by template matching, feature characterization, or frequency information such as FFT spectra, all of which are well known in the art. Fractionation may result due to increased interstitial fibrosis, progressive necrosis from a recent myocardial infarction, or changes in cell geometry. Thus, measurement of such fractionation provides a measure of myocardial state.

Wall thickness estimates may be made from the maximum negative amplitude 142 or maximum positive amplitude 144 of the evoked response. If the number of active cells (those capable of depolarizing and propagating a depolarization) are modeled as signal sources, then, as the wall thickness decreases due to changed filling or progressive dilation of the myocardium, there will be fewer cells within a few space constants or the "view" of the stimulation and sensing electrodes. With fewer such signal sources, the evoked response amplitude will be smaller since the sense electrode effectively integrates the action potentials within a few space constants of the sense electrode. Hence, as the wall thickness decreases, the evoked response amplitude will be smaller. This feature may be used for monitoring the progression of cardiac dilation in CHF, or to derive estimates of wall tension or diastolic stiffness, or even to optimize AV/PV delay.

Also, the amplitude of the evoked response is correlated to conduction velocity at the underlying cells. The intracellular resistivity of the myocardial cells is inversely related to the square of the conduction velocity. Since the transmembrane current is proportional to the spatial derivative of the intracellular current, then the transmembrane current is also proportional to the conduction velocity. Finally, the evoked response, being an extracellular potential, is therefore proportional to the conduction velocity by the integral of the transmembrane current over the volume of tissue beneath the electrode. In sum, increased conduction velocity will generate larger evoked responses. In this way, the amplitude of the evoked response may be used as a surrogate for the myocardial state.

Lastly, heterogeneity of repolarization measurements may be made using the maximum positive T-wave amplitude 146, the maximum negative T-wave amplitude 148, or the negative T-wave slope 150 of the T-wave following a captured stimulation pulse. Since the evoked response integrates the action potentials of the local cells, the homogeneity of the repolarization of these cells will be indicated by the amplitude and slew rate of the T-wave. For example, if all of the cells within the evoked response space constant repolarize in an organized fashion, both the T-wave amplitude and slope will be relatively large and smooth. However, if the cells repolarize in a more chaotic manner, the amplitude and slope of the T-wave may be reduced and/or fractionated. Such changes in amplitude and slope may be used to estimate the heart's predisposition to arrhythmia to enable the physician to titrate anti-arrhythmic drugs and/or pacing therapy or to determine the appropriate device response to a sensed premature ventricular contraction or to ready an ICD for shock delivery.

Figure 4:
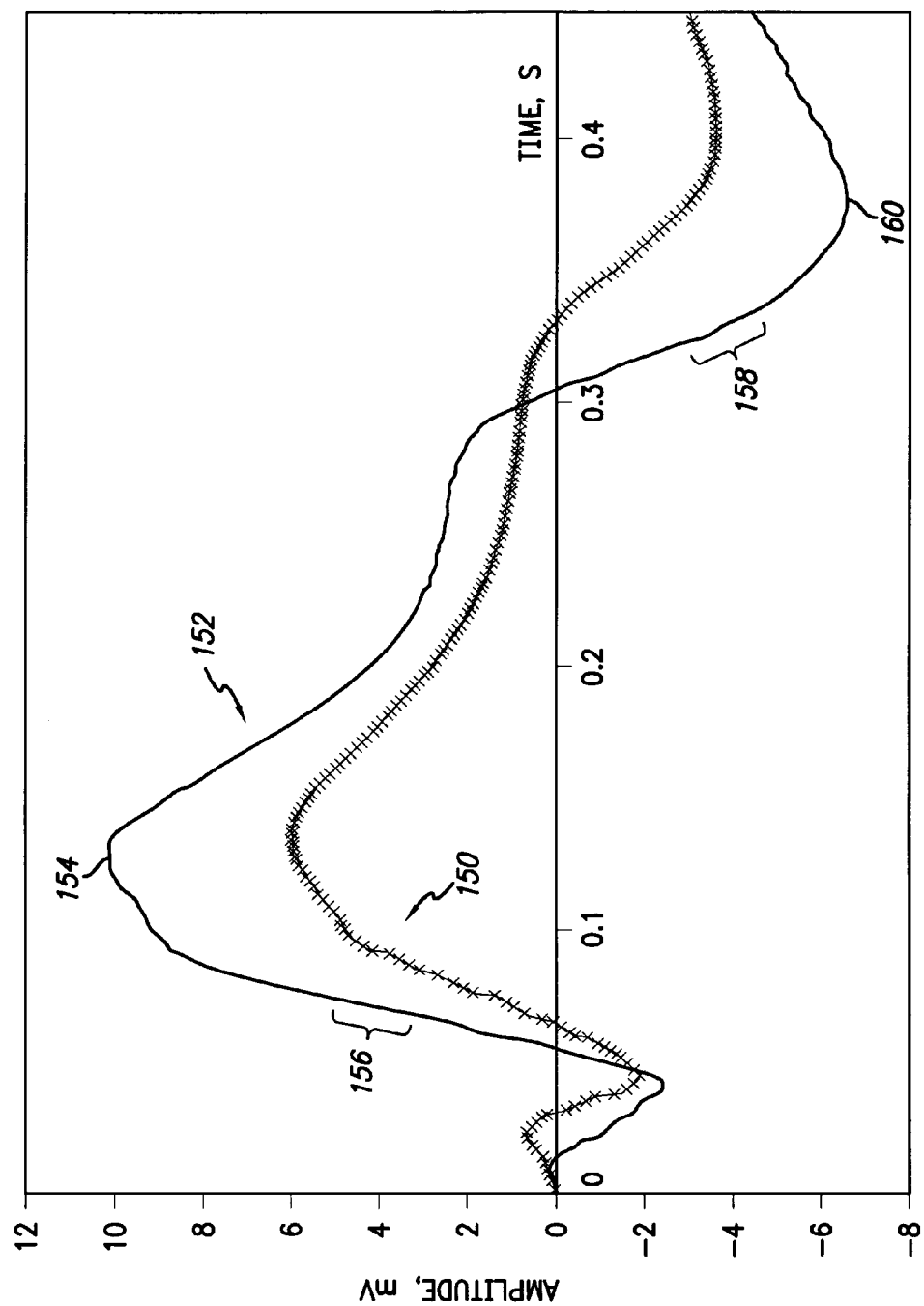
FIG. 4 illustrates an example of the changes in several features of the ventricular evoked response while in two different states of congestive heart failure, separated in time by 1 month and after treatment for CHF.

FIG. 4 shows an example of the change in several features of the ventricular evoked response for the same patient in two different states of congestive heart failure. During the first visit, the patient was fatigued, had been in chronic AF for an extended period of time, and had labored breathing. The ventricular evoked response, measured during this first visit, is shown in FIG. 4 at waveform 150. Soon after this visit, the patient became fully decompensated and was hospitalized for 1 week. While in the hospital, the patient was cardioverted; inotropic and diuretic therapy were optimized; and bed rest was mandated.

At a follow-up visit 30 days later, electrograms were again obtained. It was discovered that the patient had returned to a chronic AF condition, the onset of which occurred approximately 8 hours prior to the follow-up visit. However, the ventricular evoked response measured on the follow-up visit indicated a more robust myocardial state, as shown in FIG. 4 at waveform 152.

As can be seen in the simultaneous comparison of these two electrogram waveforms, 150 and 152, the differences in the features of the waveforms reflect the improved myocardial state: waveform 152 has a larger depolarization amplitude 154, a greater positive slope in the depolarization portion 156, and greater T-wave slope 158 and amplitude 160, when compared to waveform 150.

Figure 5:
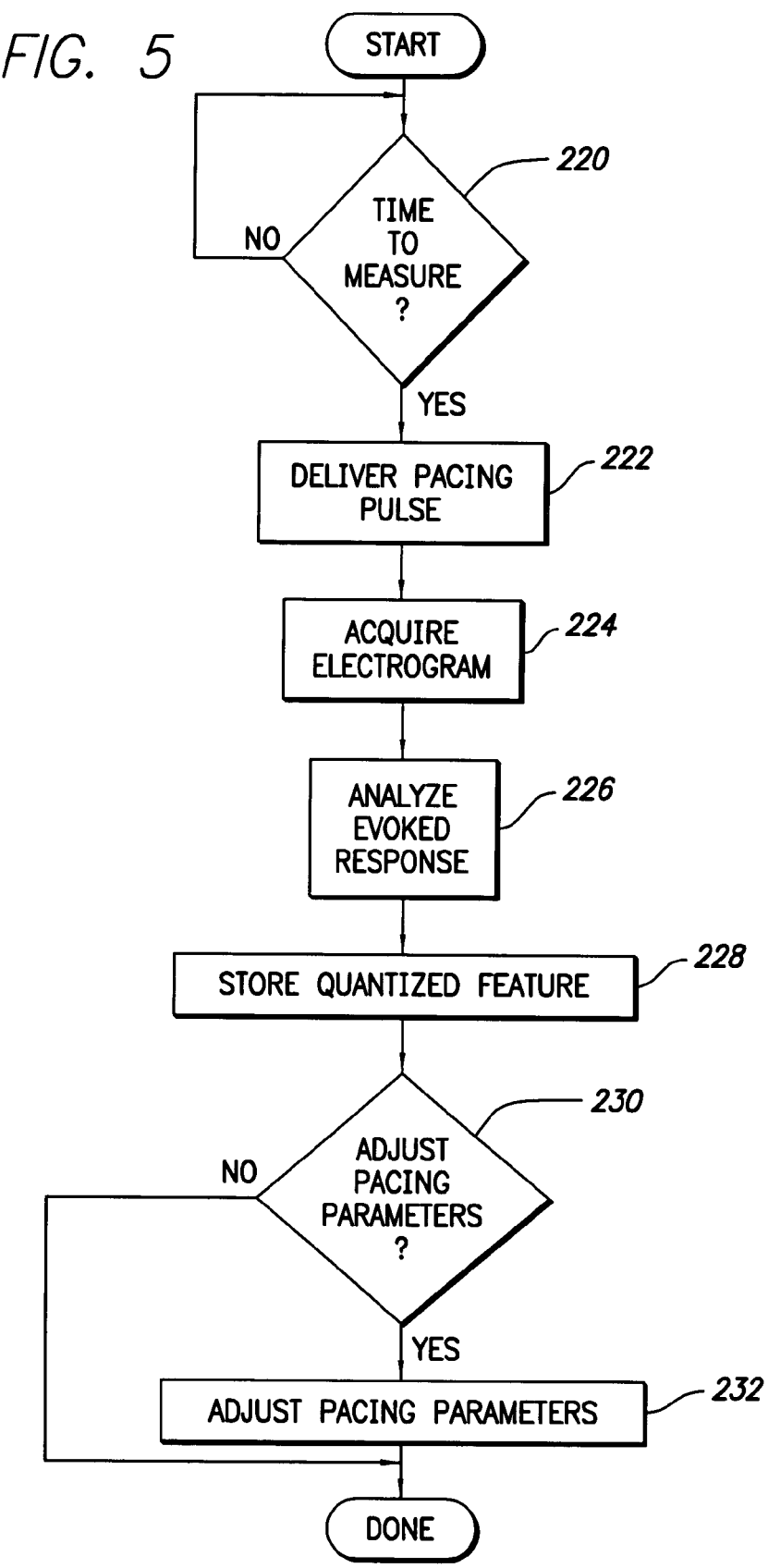
FIG. 5 is a flow chart describing an overview of the operation of a preferred embodiment of the present invention.

In FIG. 5, a flow chart is shown describing an overview of the operation and novel features implemented in the device 10 in accordance with a preferred embodiment of the present invention. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Referring now more specifically to FIG. 5, the process initiates at decision block 220 wherein the microcontroller determines if it is time to measure or quantize the given feature of an evoked response for purposes of monitoring the progression or regression of a patients heart disease. As previously mentioned, the given evoked response feature may be quantified at regular intervals as, for example, once or twice each day, or as often as on every paced and captured beat. If it is time to quantify the given evoked response feature as determined in decision block 220, the process advances to activity block 222 wherein a stimulation pulse is delivered to the appropriate chamber of the heart. As contemplated by the present invention, the evoked response of any of the ventricles or atria may be monitored. As a result, the stimulation pulse may be delivered to the right ventricle for monitoring the right ventricular evoked response, to the left ventricle for monitoring the left ventricular evoked response, to the right atrium for monitoring the right atrial evoked response, or to the left atrium for monitoring the left atrial evoked response. In addition and as previously mentioned, the measurements are preferably made utilizing a unipolar electrode configuration. As a result, if the right ventricular evoked response is to be monitored, it is preferred that the switch bank selects the right ventricular tip terminal 52 and the case 40 for both delivery of the stimulation pulse and the sensing of the evoked response. If the left ventricular evoked response is to be monitored, the switch bank preferably selects the left ventricular tip terminal 44 and the case 40 for both the delivery of the stimulation pulse and the sensing of the evoked response. If the right atrial evoked response is to be monitored, the switch bank preferably selects the right atrial tip terminal 42 and the case 40 for both the delivery of the stimulation pulse and the sensing of the evoked response. Lastly, if the left atrial evoked response is to be monitored, the switch bank preferably selects the left atrial ring terminal 46 and the case 40 for both the delivery of the stimulation pulse and the sensing of the evoked response.

Once the stimulation pulse is delivered to, for example, the right ventricle, in accordance with activity block 222, the process advances to activity block 224 wherein the microcontroller causes the data acquisition system 90 to acquire the electrogram of the evoked response. The microcontroller immediately stores the evoked response signal generated by the data acquisition system 90 in the memory 94.

Once the evoked response is stored, the process advances to activity block 226 wherein the evoked response is analyzed. In accordance with activity block 226, the evoked response is analyzed for isolating the selected feature to be quantified and for quantifying the selected feature. As previously mentioned, the selected feature may be the positive slope of the evoked response, the continuity of the evoked response, the amplitude of the evoked response, the amplitude of the T-wave, or the slope of the T-wave. Once the evoked response selected feature is quantified, the quantized feature value is stored in the memory 94 in accordance with activity block 228.

The process now advances to decision block 230. In accordance with decision block 230, the microcontroller determines if the pacing parameters require adjustment commensurate with the relative changes in or the trend of the quantified evoked response feature values which have been stored over time. If the quantified evoked response feature values indicate that remodeling of the heart has occurred, the microprocessor may determine that adjusting pacing parameters is not required at this time, where upon, the microcontroller immediately returns. However, if the quantified evoked response feature values indicate that pacing parameter adjustment is advisable, the microcontroller then advances to activity block 232 wherein the pacing parameters are suitably modified. For example, if the quantified evoked response feature values indicate that repolarization has become less heterogeneous, indicating that successful reverse remodeling has occurred, the device may be programmed as, for example, to adjust the interventricular delay in the case of biventricular pacing to enhance hemodynamics or, in the case of single chamber pacing, to reduce the pacing rate or lengthen the AV delay to increase intrinsic activity of the heart and decrease pacing intervention. After adjusting the pacing parameters, if appropriate, in accordance with activity block 232, the process returns.

In addition to the foregoing, in a multisite pacing system, independent evoked response feature measurement may be made to indicate the uniformity of the myocardial state across the heart. For example, the device may pace each chamber independently and quantify the evoked response features. For example, if a biventricular pacing system is implemented, the right ventricular myocardium may be characterized by pacing only the right ventricle and analyzing the right ventricular evoked response and similarly, pacing the left ventricle only and analyzing the left ventricular evoked response. Such measures may be compared to previously obtained estimates or under different pacing conditions and used to optimize pacing parameters or guide physician administered therapy.

As an example of the above, immediately upon implant of a biventricular pacing system, the left ventricular evoked response and right ventricular evoked response are measured. If, for example, they indicate widely different repolarization characteristics, then biventricular pacing may be established with an interventricular delay of, for example, 0 milliseconds. At a later date, perhaps a month, the left ventricular evoked response and right ventricular evoked response measurements are obtained again when repolarization parameters are now more uniform, indicating that successful reverse remodeling of the heart has been accomplished by the pacing therapy. The physician might now adjust the therapy or, the device could be programmed to search for a different interventricular delay to enhance hemodynamics. The foregoing could also apply to biatrial pacing where homogeneity of the right atrial evoked response and the left atrial evoked response could be used to titrate the aggressiveness of pacing therapy, for example, DAO pacing therapy.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described.

What is claimed is:

1. A method for monitoring a progression or regression of congestive heart failure, the method comprising:
   applying stimulation pulses to a heart;
   sensing electrical evoked responses and providing corresponding evoked response signals;
   processing the evoked response signals and generating a value for at least one characteristic of the evoked response signals, the at least one characteristic comprising at least one of a positive slope in the evoked response signals, a continuity in the evoked response signals, and a T-wave slew rate in the evoked response signals;
   monitoring the values as a function of time to obtain a trend and to determine if progression or repression of congestive heart failure exists; and
   adjusting pacing parameters commensurate with relative changes in the trend if progression or regression of congestive heart failure exists.

2. The method of claim 1 wherein adjusting pacing parameters comprises adjusting the pacing parameters if the trend indicates that remodeling of the heart has occurred.

3. The method of claim 1 wherein processing comprises quantifying the positive slope in the evoked responses signals.

4. The method of claim 1 wherein processing comprises quantifying the continuity in the evoked response signals.

5. The method of claim 1 wherein processing further comprises quantifying maximum amplitudes in the evoked response signal.

6. The method of claim 1 wherein processing comprises quantifying the T-wave slew rates in the evoked response signals.

7. The method of claim 1 wherein processing further comprises quantifying a T-wave amplitude in the evoked response signals.

8. A cardiac stimulation system that monitors for a progression or regression of congestive heart failure, the system comprising:
   a pulse generator that generates pacing pulses to be delivered to the heart;
   at least one lead to deliver the pacing pulses to the heart, to sense electrical evoked responses of the heart, and to generate evoked response signals; and
   control circuitry that is in communication with the at least one lead, wherein the control circuit processes the evoked response signals to generate quantized values for at least one characteristic of the evoked response signals, wherein the control circuitry processes the quantized values as a function of time to obtain a trend and to determine if progression or regression of congestive heart failure exists, and wherein the at least one characteristic comprises at least one of a positive slope in the evoked response signals, a continuity in the evoked response signals, and a T-wave slew rate in the evoked response signals;
   wherein the system comprises an external programmer, and wherein the control circuitry is housed in the programmer.

9. A system that monitors for a progression or regression of congestive heart failure, the system comprising:
   means for applying stimulation pulses to the heart;
   means for sensing electrical evoked responses of the heart;

means for processing the electrical evoked responses and providing corresponding evoked response signals, the evoked response signals comprising at least one of a positive slope in the evoked response signals, a continuity in the evoked response signals, and a T-wave slew rate in the evoked response signals;

means for analyzing the evoked response signals as a function of time; and means for determining if progression or regression of congestive heart failure exists based on the means for analyzing; and means for adjusting pacing parameters commensurate with relative changes in the trend if progression or regression of congestive heart failure exists.

10. A cardiac stimulation system that monitors for a progression or repression of congestive heart failure, the system comprising:

a pulse generator that generates pacing pulses to be delivered to the heart;

at least one lead to deliver the pacing pulses to the heart, to sense electrical evoked responses of the heart, and to generate evoked response signals; and control circuitry that is in communication with the at least one lead, wherein the control circuit processes the evoked response signals to generate quantized values for at least one characteristic of the evoked response signals, wherein the control circuitry processes the quantized values as a function of time to obtain a trend and to determine if progression or repression of congestive heart failure exists, and wherein the at least one characteristic comprises at least one of a positive slope in the evoked response signals, a continuity in the evoked response signals, and a T-wave slew rate in the evoked response signals;

wherein the control circuitry adjusts pacing parameters commensurate with relative changes in the trend if progression or regression of congestive heart failure exists.

11. The cardiac stimulation system of claim 10 wherein the control circuitry adjusts pacing parameters if the trend indicates that remodeling of the heart has occurred.

12. The cardiac stimulation system of claim 10 wherein the system comprises an implantable cardiac stimulation device, and wherein the pulse generator and control circuitry are housed in the implantable cardiac stimulation device.

13. The system of claim 10 wherein the at least one characteristic further comprises maximum amplitudes in the evoked response.

14. The system of claim 10 wherein the at least one characteristic further comprises a T-wave amplitude in the evoked response.

15. The system of claim 10 wherein the at least one lead delivers pacing pulses to the right ventricle of the heart.

16. The system of claim 10 wherein the at least one lead delivers pacing pulses to the left ventricle of the heart.

17. The system of claim 10 wherein the at least one lead delivers pacing pulses to the right atrium of the heart.

18. The system of claim 10 wherein the at least one lead delivers pacing pulses to the left atrium of the heart.

* * * * *